(12) United States Patent
Schroeder

(10) Patent No.: US 9,037,269 B2
(45) Date of Patent: May 19, 2015

(54) APPLICATOR HEAD AND METHOD FOR TREATMENT OF PAIN BY TRANSCUTANEOUS ELECTRICAL NERVE STIMULATION

(71) Applicant: Norman R. Schroeder, Jefferson City, MO (US)

(72) Inventor: Norman R. Schroeder, Jefferson City, MO (US)

(73) Assignee: N & C Holdings, LLC, Jefferson City, MO (US)

( * ) Notice: Subject to any disclaimer, the term of this patent is extended or adjusted under 35 U.S.C. 154(b) by 0 days.

(21) Appl. No.: 13/966,342

(22) Filed: Aug. 14, 2013

(65) Prior Publication Data

US 2015/0051685 A1    Feb. 19, 2015

(51) Int. Cl.
*A61N 1/18*     (2006.01)
*A61N 1/40*     (2006.01)
*A61N 1/36*     (2006.01)
*A61N 1/04*     (2006.01)

(52) U.S. Cl.
CPC .......... *A61N 1/36021* (2013.01); *A61N 1/0456* (2013.01)

(58) Field of Classification Search
USPC ............ 607/45, 46, 48, 50, 51, 115, 145–151
See application file for complete search history.

(56) References Cited

U.S. PATENT DOCUMENTS

| | | | |
|---|---|---|---|
| 2,327,874 A | 8/1943 | De Jong | |
| 4,033,356 A * | 7/1977 | Hara | ............................ 607/152 |
| 4,381,012 A | 4/1983 | Russek | |
| RE32,091 E * | 3/1986 | Stanton | ........................... 607/48 |
| 5,251,637 A * | 10/1993 | Shalvi | ........................... 600/548 |
| 5,304,207 A * | 4/1994 | Stromer | ........................... 607/3 |
| 5,314,423 A | 5/1994 | Seney | |
| 5,578,065 A | 11/1996 | Hattori et al. | |
| 5,643,332 A | 7/1997 | Stein | |
| 5,759,198 A | 6/1998 | Karell | |
| 5,800,477 A | 9/1998 | Groux | |
| 5,913,836 A | 6/1999 | Groux | |
| 6,026,327 A * | 2/2000 | Dervieux | ........................ 607/46 |
| 6,366,813 B1 | 4/2002 | DiLorenzo | |
| 6,801,808 B2 * | 10/2004 | Lee | ................................ 607/76 |

(Continued)

FOREIGN PATENT DOCUMENTS

| | | |
|---|---|---|
| DE | 102008039387 A1 | 3/2010 |
| EP | 1359971 A2 | 11/2003 |
| WO | 01/91849 A1 | 12/2001 |

OTHER PUBLICATIONS

European Search Report and Written Opinion from co-pending European Patent Application No. 14180949.1, filed Aug. 14, 2014.

(Continued)

*Primary Examiner* — Brian T Gedeon
(74) *Attorney, Agent, or Firm* — Grace J. Fishel

(57) ABSTRACT

Embodiments of the present invention include an apparatus and method for treatment of pain by a device that provides transcutaneous electrical nerve stimulation. The device includes an applicator equipped with an electric pulse provider that sends an electric pulse to a set of electrodes disposed in an applicator head. The device is placed onto the skin of a patient's body at the point where the patient experiences pain and such that the electrodes of the device contact the skin of the patient while an insulating land area between the electrodes compresses the nerve during transmittal of the electric pulse through the electrodes and into the patient's body.

14 Claims, 2 Drawing Sheets

(56) References Cited

U.S. PATENT DOCUMENTS

| | | |
|---|---|---|
| 6,845,264 B1 | 1/2005 | Skladnev et al. |
| 7,613,517 B2 | 11/2009 | Goroszeniuk |
| 7,769,473 B2 | 8/2010 | Axelgaard |
| 8,014,876 B2 * | 9/2011 | Colthurst ................... 607/145 |
| 8,588,918 B2 * | 11/2013 | Bighetti ...................... 607/46 |
| 2003/0176822 A1 | 9/2003 | Morgenlander |
| 2004/0243197 A1 | 12/2004 | Demian |
| 2006/0178706 A1 | 8/2006 | Lisogurski et al. |
| 2008/0208284 A1 | 8/2008 | Rezai et al. |
| 2009/0221943 A1 | 9/2009 | Burbank et al. |
| 2009/0312826 A1 | 12/2009 | Penny et al. |
| 2010/0160712 A1 | 6/2010 | Burnett et al. |
| 2010/0249637 A1 | 9/2010 | Walter et al. |
| 2011/0202121 A1 | 8/2011 | Wen |
| 2012/0209340 A1 * | 8/2012 | Escribano ....................... 607/3 |

OTHER PUBLICATIONS

LexisNexis Total Patent Translation of DE 10 2008 039387.

* cited by examiner

APPLICATOR HEAD AND METHOD FOR TREATMENT OF PAIN BY TRANSCUTANEOUS ELECTRICAL NERVE STIMULATION

FIELD OF THE INVENTION

This disclosure relates to the field of treatment of pain, and more specifically, to a TENS unit with a specially configured applicator head and to the more effective treatment of pain using that applicator head.

BACKGROUND OF THE INVENTION

This section provides general background information related to the present disclosure and is not necessarily prior art.

Countless people suffer from chronic, intermittent, or injury related pain. Often the body responds to pain by tightening the muscles which can decrease the circulation in the affected area and cause the patient continuing painful symptoms.

It is noted that pain is a warning system and is the human body's primary method of telling a person that something is wrong. Pain is important because without it, abnormal conditions may go undetected, and that can cause significant, and sometimes permanent, damage or injury to vital body parts.

It is estimated that about 25% of the population suffers from chronic pain. Several major medical institutions have also estimated that about 8-11% of the population suffer from Restless Leg Syndrome (RLS). Additionally, it is also known that about 2-3% of the population has Sciatica and another 2-3% suffer from Fibromyalgia.

There is a long history of using electrical stimulation for relief of pain beginning with the ancient Egyptians and Greeks who knew of the electro-analgesic effects of standing in a pool with electric fish. In more recent times, low voltage pulses of electric current for pain relief became popular with the U.S. military during World War II.

Since 1960 and the advent of the microelectronic age, transcutaneous electrical nerve stimulation medical devices have become smaller and more portable. Over the past 60 years, such devices have become the preferred choice for non-addictive drug free control of pain for millions of people.

Traditionally, transcutaneous electrical nerve stimulation makes use of flexible electrodes that are attached to the skin or the use of electrical probes having a variety of shapes and sizes. These devices all rely on a stimulating pulse current that travels between an anode through the skin into the underlying tissues and back though the skin to a cathode.

The problem with this arrangement is that the current is diffused or diluted as it expands into the various tissues of the body having different resistivities. As predicted by Ohm's law (I=V/R), electricity takes the path of least resistance. If the electrode is pressed directly over the nerve as current TENS units describe, the results are unpredictable and ambiguous because of the variable resistance of the skin, tissue and nerve. The effectiveness of the treatment of any given nerve center is dependent on the amount of current that actually reaches all the symptomatic portions of a particular nerve and this explains the erratic nature of the results when using prior art devices.

Therefore, there is a need to provide a more predictable method of treating pain that includes a specially designed treatment device that can be easily positioned and repositioned to effectively treat a nerve that is suspected of being the source of a patient's pain.

SUMMARY OF THE INVENTION

This section provides a general summary of the disclosure, and is not a comprehensive disclosure of its full scope or all of its features. More specifically, embodiments of the invention as disclosed and discussed herein relate to an improved TENS unit which can be used to more effectively treat pain such as results from minor and severe muscle strains, Restless Leg Syndrome, Sciatica and Fibromyalgia.

Aside from its value in diagnosis, long-lasting persistent pain serves no useful purpose. Pain starts as a signal from a distressed biological component which is passed along the network of nerves to the brain where it the signal is decoded, analyzed, and then reacted to. More specifically, the pain signal travels from the injured area along the small nerves leading to the spinal cord where the signal is switched or routed to other nerves that connect the spinal cord to the brain. The brain then interprets the pain signal as an indication of "pain." That feeling of "pain" is the source of the discomfort and hurt felt by a patient. Various embodiments of the present invention interrupt these electrical nerve signals at the source and relieve the patient's "pain."

Therefore, in accordance with the various embodiments of the present invention as disclosed and discussed herein, various embodiments of the present invention include a battery powered non-invasive, non-addictive, drug free TENS unit with an improved applicator head that works in a similar manner as a spinal stimulator to control pain, except that the present stimulation device does not penetrate the skin or require implantation. The applicator head is unique in that when it is pressed against the body, the rectangular electrodes and the insulating land in between the electrodes compress the body tissue to create an electrical pathway in which the painful nerve center is captured and compressed. The shape of the electrodes and the insulating land and the electrical properties of body tissue work together to focus the gentle pulses of current directly through the compressed nerve to more effectively suppress the sensation of pain in underlying nerves. This numbing of the nerve may last for 8-36 hours depending on treatment time, severity of symptoms and variations between patient conditions. Often, as a result of the relaxation of nearby muscle tissue caused by gentle massaging with the applicator head, the pain cycle is interrupted on a permanent basis and the pain will not return.

More specifically, various embodiments of the present invention only require the simple pressing of the TENS unit applicator head with electrodes flanking an insulating land on the outer surface of a patient's body by the patient at the area where the patient experiences pain without the assistance of specialized medical personnel. The block insulator focuses the current through the nerve in a manner that maximizes the effective current to the nerve and "patient usability" is enhanced by use of a very low current that greatly reduces the possibility of burns to the patient's skin. Nerves which lie deep within the body such as those associated with RLS, chronic pain, and strained muscles, can be quickly desensitized with treatment times that last only a few seconds.

Additionally, certain embodiments of the present invention may be used by emergency personnel treating patients with severely painful strained muscles with dramatic results in less than a minute. Embodiments of the present invention can be used on older patients without significant risk of interference to heart rhythms or pacemakers. RLS patients can also use certain embodiments of the present invention before retiring or sitting to eliminate the leg jerking that can cause discomfort and serious sleep disorders. Patients that suffer from Fibromyalgia can either eliminate or greatly reduce their symptoms with self treatment on a daily basis. Immobilized or bedridden patients with Sciatica may be able to walk normally again and lead normal lives.

It is noted that various embodiments of the present invention incorporate a TENS unit applicator head having a flat block insulator or insulating land located between two essentially parallel electrodes. When the insulator portion is pressed down over the nerve, the nerve is compressed thus allowing the electrical current to be focused precisely below the insulating land and through the compressed nerve directly below the land and skin. This cannot be done with prior art flexible electrodes or probes because without the insulating land, the nerve will not be compressed and without nerve compression, the current from the electrodes will pass through only a small portion of the nerve.

With prior art TENS units the individual electrodes are usually widely-placed over the body of a patient. With this kind of electrode placement, the current density is uncontrollable and the path is unpredictable because the nerves are not in a compressed state and the current path does not reach the entire nerve. Current is either diluted before it reaches the symptomatic nerve giving rise to the pain signals or the current will follow a vein or artery from one electrode to the other and miss the nerve entirely. On the other hand, if the two electrodes are placed a short distance from each other, current flows just below the uncompressed skin and does not reach the distressed nerves lying deeper within the patient's body.

Thus, if one electrode of prior art TENS units is simply placed over the nerve, the current path may be to one side, straight down, or to a large blood vessel depending on resistivity of the skin, tissue and nerve—any of which can prevent focus of current to the nerve. As a result such electrotherapy treatment methods require lengthy treatment times of many hours or all day because of the dilution or diffusion of the electrical current or are completely ineffective.

In the various embodiments of the present invention, the use of the block insulator or insulating land compresses the nerve and focuses the current through the compressed nerve below the insulating land. More particularly with the present invention, there is a laminar flow of current passing between the electrodes under the block insulator just below the skin and through the compressed nerve. This greatly decreases the treatment time and greatly increases the effectiveness of treatment using transcutaneous nerve stimulation and because of the present embodiment's greater efficiency, also allows the use of lower skin currents for safer operation and treatment.

As is more particularly described below, the cross sectional area of the current pathway under the block insulator is also many time less than the cross sectional area of the individually placed electrodes. This allows for a focused laminar flow of electrical current under the skin and through the entire nerve which is compressed under the land. The laminar current flow evenly distributes the current throughout that part of the nerve that is compressed under the insulating block. Due to the laminar current flow through the nerve, the patient can feel the silhouette and location of the nerve center during treatment. This allows the patient to immediately make intuitive judgments as to the best placement of the electrodes in the applicator head. A patient can initially determine the exact location of the painful nerve caused by chronic pain, muscle strains, RLS, Fibromyalgia or Sciatica by pressing a finger on and around the nerve that is the suspected source of the pain. The same results can be obtained by pressing the center of the insulating block to the nerve area while applying power to determine the location of the nerve sensation that is felt during treatment.

The amplifying effect of current on the treatment of the nerve area compressed under the insulative land may be analogized to the power from an FM radio transmitter which may have an output of 6,000 watts to the antenna, but the antenna has an output of 30,000 watts of effective power. This amplification occurs because radio frequency energy from the radio's transmitter is redirected by the antenna into the electromagnetic medium in a focused manner. Similarly, a flashlight may be rated at 1,000,000 candlepower while the bulb in the flashlight is only a fraction of that amount. The parabolic mirror of the flashlight focuses the bulb to become 1,000,000 candlepower. Similarly, nerves are three dimensional and spread out over a given area, but when they are compressed into an essentially flat plane, the treatment current is focused through the same flat plane and the entire selected area of the nerve can receive a uniform current flow with much faster and far greater desensitization of the nerve. It is this "amplifying effect" that assists the embodiments of the present invention to have increased effectiveness in pain treatment by transcutaneous electrical nerve stimulation.

For larger nerves, after the initial treatment, the patient can re-position the block to either side of the larger nerve for treatment of the entire nerve. In preferred embodiments, the insulating block and flanking electrodes are assembled into a treatment applicator as a single unit and the battery operated power supply can be located in the handle of the applicator.

In accordance with the various embodiments of the present invention, this invention relates to an apparatus and method for treatment of pain by transcutaneous electrical nerve stimulation. Further areas of applicability will become apparent from the description provided herein. The description and specific examples in this summary are intended for purposes of illustration only and are not intended to limit the scope or the claims of the present disclosure.

DESCRIPTION OF THE DRAWINGS

In the accompanying drawings which form part of this specification.

Corresponding reference numerals indicate corresponding steps or parts throughout the several figures of the drawings.

DETAILED DESCRIPTION OF AT LEAST ONE EMBODIMENT OF THE INVENTION

Figure 1:
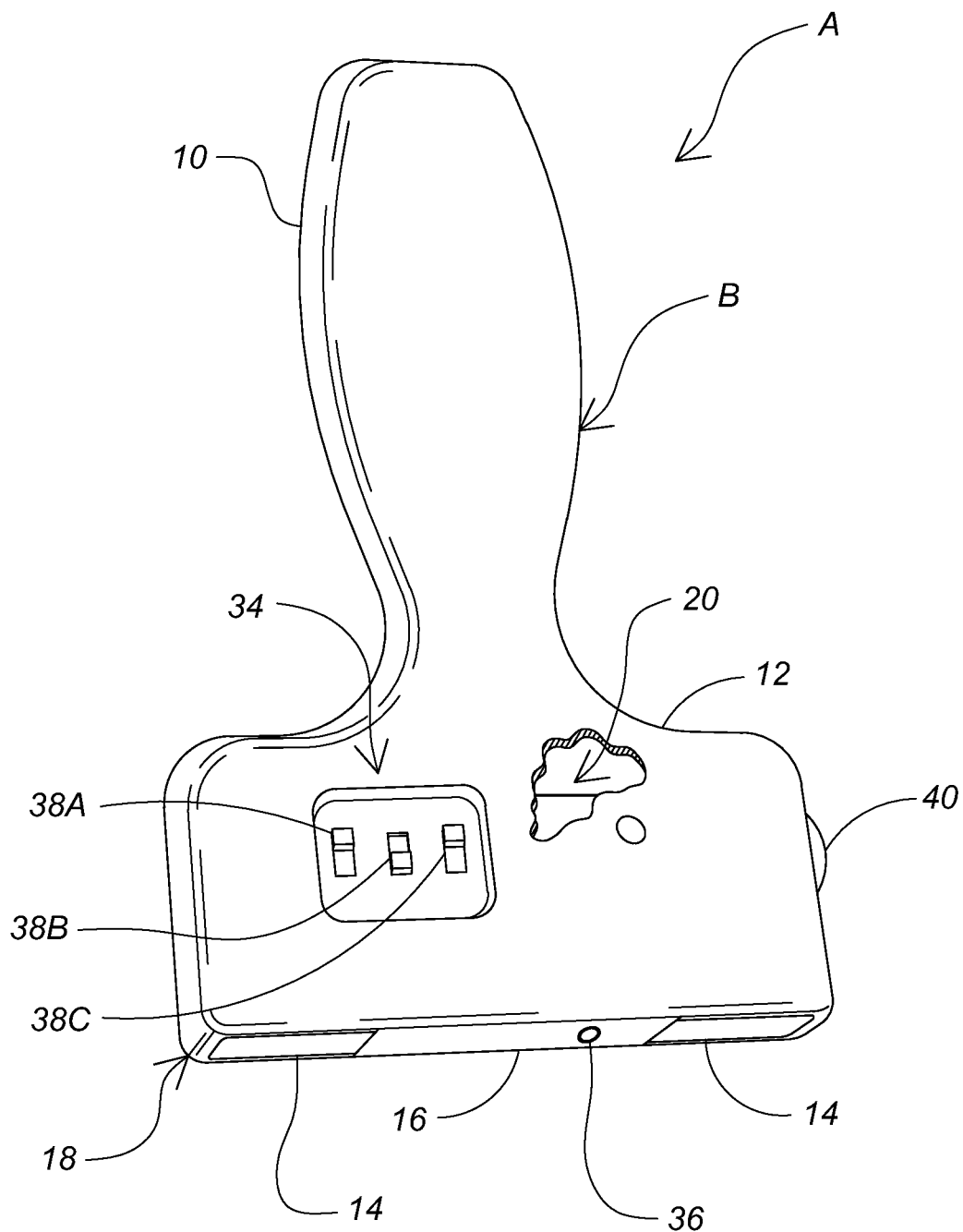
FIG. 1 shows a perspective view of one embodiment of a TENS unit with an applicator head in accordance with the present invention.

In the following description, numerous specific details are set forth such as examples of some embodiments, specific components, devices, methods, in order to provide a thorough understanding of embodiments of the present disclosure. It will be apparent to a person of ordinary skill in the art that these specific details need not be employed, and should not be construed to limit the scope of the disclosure. In the development of any actual implementation, numerous implementation-specific decisions must be made to achieve the developer's specific goals, such as compliance with system-related and business-related constraints. Such a development effort might be complex and time consuming, but is nevertheless a routine undertaking of design, fabrication, and manufacture for those of ordinary skill.

An embodiment of the present invention is illustrated in the drawings and figures contained within this specification.

Referring now to FIG. 1, an embodiment of the improved TENS unit A comprises an applicator B that includes a handle 10 with a paddle portion 12. A set of two electrodes 14 separated by an insulative land or block insulator 16 is provided in a head 18 of applicator B. In alternative embodiments of the present invention, handle 10 and paddle portion 12 can be manufactured from plastic, wood, or any other material as long as the material selected is an electrically insulating material. For example, a polystyrene plastic material could be used and still remain within the scope of the present invention. It will be understood that applicator B may be of any shape as long as the handle allows a user to be able to comfortably grip the device for a period of about 15 minutes, and as long as the applicator head 18 allows at least one surface of electrodes 14 and insulative land 16 to be coplanar such that they readily contact the skin surface of a patient during treatment with the improved TENS unit A.

The electrodes 14 of a preferred embodiment are made from an electrically conducting material. In the present embodiment, the two electrodes 14 are made from medical grade stainless steel. In alternative embodiments, the electrodes 14 are made from electrically conductive metal such as zinc, steel, or other conductive material which is harmless to the body. It is understood by those of skill in the art that the set of two electrodes 14 is conductively attached to an electrical connection point, with one electrode being in electrical contact to an positive terminal and the other electrode is electrically connected to a negative terminal such that a DC current can flow between electrodes 14 if the two electrodes were conductively connected.

The subject embodiment of the improved TENS unit A includes an electric pulse provider 20 that is generally disposed within the handle 10. In alternative embodiments, the electric pulse provider 20 may be located separately from the handle 10 and then electrically connected to the improved TENS unit A by electrical conductors.

Figure 2:
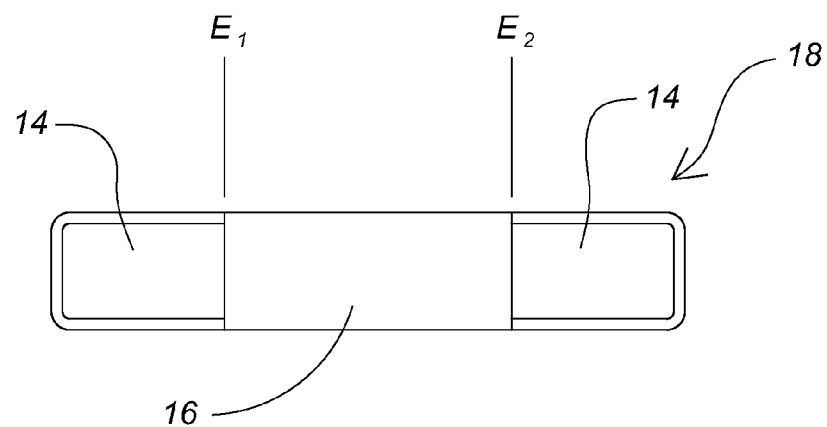
FIG. 2 shows an end view of the applicator head for one embodiment of the present invention.
Figure 3:
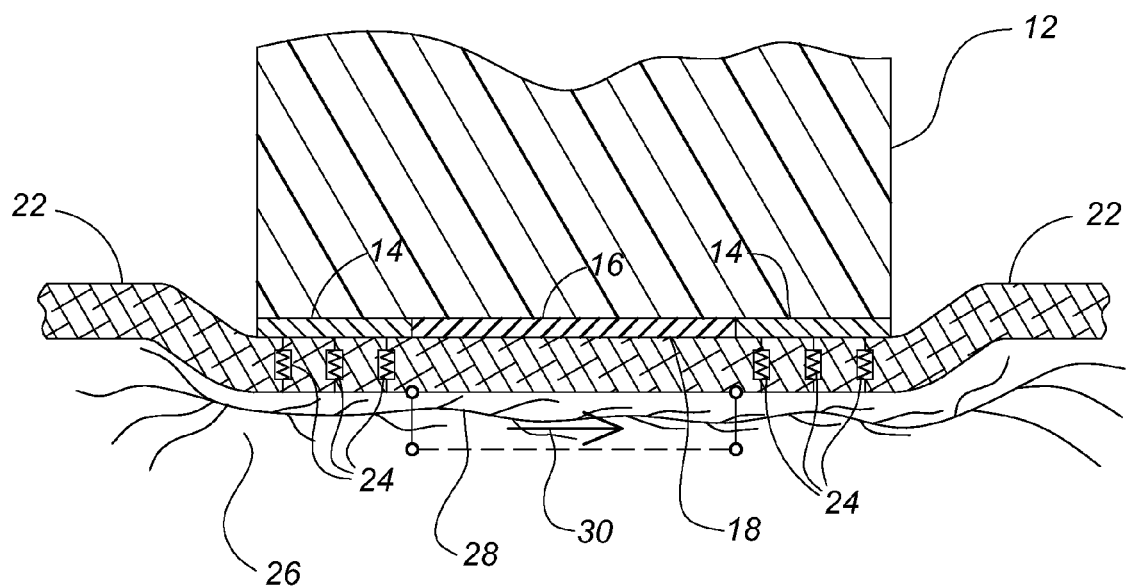
FIG. 3 shows a pictorial representation of a cross-section of the applicator head showing how the electric current is applied to the patient's body during use of one embodiment of the present invention.

As shown in FIGS. 2 and 3, electrodes 14 flank insulative land 16. In a preferred embodiment, the skin contacting portion of each electrode measures 1.65 cm (0.65 in) by 2.54 cm (1.0 in) and has an area of 4.19 cm$^2$. The insulative land 16 measures 3.30 cm (1.3 in) by 1.65 cm (0.65 in). It is noted that human skin has a resistance of roughly 6,000 ohms/cm$^2$. The resistivity of skin on electrodes 14 is pictorially represented in FIG. 3 by indicating one 6,000 ohm resistor for each square centimeter of the electrode surface.

In contrast, flesh 26 beneath skin 22 has very low resistance compared with the skin. This resistance varies but is about 5-40 ohms/cm$^2$. Resistors 24 are connected to flesh 26. Electrons passing from the cathode to the anode will take the path of least resistance, that pathway under land 16 being a laminar flow of electrons through flesh 26 below skin 22. With the electric pulse providers 20 as described below, the current pathway beneath land 16 is about 0.2 cm (0.08 in) to about 0.7 cm (0.28 in) deep and the area of the pathway 30 is 0.3 cm$^2$. Electrons from the cathode 14 having an area of 4.19 cm$^2$ are funneled through the current pathway under the land 16 having an area of 0.3 cm$^2$ resulting in a current density theoretically 14 times greater than the current density from the electrode. This improvement in current density makes it possible to operate improved TENS unit A at lower skin currents for safer operation and treatment. While the theoretical increase in current density could be as high as 14, in practice it will be less because not all of the current will be perfectly channeled through the compressed area under land 16 but conservatively the increase in current density will in the order of 2 to 5 times the current density coming from the cathode.

The current density in the pathway 30 can be increased by lengthening the electrodes 14. For example, if the length of the electrode is doubled to 5.08 cm and the width remains 1.65 cm, the area of the electrode would double to 8.38 cm$^2$ but the area of current pathway 30 would remain the same. The ratio between the current pathway 30 area and the electrode 14 area is 8.38/0.3 and the theoretically the gain in current density under the land would be 28. The width of the electrode is not a factor in this formula because any change in width will affect the pathway area by the same factor and the current gain ratio will remain the same.

There is a practical limit on the length of the electrodes 14 as the total area of the electrodes 14 and the length of land 16 determines the amount of force required to compress and flatten the nerve 28 under the land 16. It is preferred that the spacing between electrodes 14 and length of land 16 be between about 8.89 cm (3.5 in) and 1.27 cm (0.5 in). If the land is longer than about 3.5 inches, there is a detrimental effect on the laminar flow of the electrons thus reducing the current density and the effectiveness of the treatment because it is difficult to flatten the treatment area over that length. On the other hand, if the land is shorter than about 1.25 cm (0.5 in), the current flow will tend to be on the surface of the skin and not under the skin. This is due to the resistance of the surface of the skin being in parallel with the resistance from the electrode down through and under the insulating land and skin. If the resistance across the surface of the skin is R1 and resistance through the skin and under the land and skin is R2, the parallel resistance formula R1R2/(R1+R2) will be the determining factor in the path of least resistance for land lengths of less than 0.5-1 inch. With increasingly shorter land length, at some point, the path of least resistance is across the surface of the skin with little or no current flowing under the skin, thereby losing therapeutic effect.

While the specifics of a preferred embodiment are given above, the electrodes 14 may have a length between about 0.635 cm (0.25 in.) and 6.35 cm (2.5 in.) Dimensions below about 0.25 in. may not provide enough current density and dimensions above about 2.5 in. make it difficult to apply enough pressure on the treatment area as discussed below. The width of electrodes 14 may be between about 0.328 cm (0.125 in.) and 6.35 cm (2.5 in.). While the width of electrodes 14 does not affect the current density, if the electrodes 14 are too wide it may be difficult to apply effective pressure to the treatment area. The width of the insulative land 16 preferably matches the width of electrodes 14 but may be wider than the electrodes but preferably not narrower. While not shown in the drawings, it is possible that a plurality of applicators B may be grouped together for treatment of a larger area.

With continuing reference to FIG. 3, a second key to the high efficiency of improved TENS unit A is that the nerves 28 under the land 16 and electrodes 14 are compressed and flattened. By flattening the branches of the nerves 28, the nerve is placed in the dense current pathway. Regular TENS units with electrodes in a flexible pad or in a probe do not compress the nerves between the electrodes and therefore much of the current does not reach the nerve fibers. As a result, poor results are often obtained or it may take hours to desensitize the nerves.

Those of skill in the art will also appreciate the fact that the edges of each electrode 14, $E_1$ and $E_2$ of FIG. 2, may tend to work better in some instances if those nearest edges are parallel. Thus, in certain preferred embodiments, the edges of the electrodes 14 that are closest together on applicator head 18 are positioned to be parallel. The current pathway through the tissue under the land 16 is thus made constant across the width of electrodes 14.

The electric pulse provider 20 provides an electrical pulse that is transmitted to the set of electrodes 14. In the present embodiment, the electric pulse provider 20 has the following specifications:

| | |
|---|---|
| Peak Current | 0 - 80 milliamps (500 Ohms) |
| Average Current | 0 - 0.80 milliamps (500 Ohms) |
| Pulse Rate | 40 Hz |
| Pulse Width | 150 or 250 microsecond (selectable) |
| Waveform | Asymmetrical bi-phase square pulse |
| Peak Voltage | 0 - 40 Volts (500 Ohms load) |
| Maximum Charge Per Pulse | 20 microcoulombs |
| Power Supply | 9 volt battery (alkaline) |

In other embodiments, the above specifications for the electric pulse provider 20 may be adjusted as needed to reap the best benefit as necessary depending upon the type of pain being treated as long as the electric pulse provider selected is capable of performing as described herein.

For use in improved TENS unit A, the electric pulse provider 20 of the present embodiment includes an intensity control 32 for adjusting the pulse amplitude, and an array of selector switches 34. The circuitry for electric pulse provider 20 may be either analog or digital.

In another alternative embodiment, the improved TENS unit A includes an internal safety interlock switch 36 that is activated by pressing the paddle portion 12 with applicator head 18 against the patient's leg or other body part. When the safety interlock switch 36 is activated, it allows the voltage from the electric pulse provider 20 to be transmitted to the electrodes 14. It is understood by those of skilled in the art that the design, activation style, and location of the interlock safety switch 36 on the improved TENS unit A may be of any appropriate design as required to meet the unique specifications and applications of alternative embodiments of the present invention, and as long as no power is transmitted to the electrodes 14 until the interlock safety switch 36 detects applicator head 18 is being pressed against a patient's leg or other body part. In present embodiment, the array of selector switches 34 includes an ON/OFF switch 38A a pulse width switch 38B, and a voltage selection switch 38C. The present embodiment also includes an intensity control 40 on the side of the paddle 12 that can rotated to either increase or decrease the voltage intensity applied to the patient during treatment.

In alternative embodiments of the improved TENS unit A, a standby-off switch (not shown) may be included. The standby-off switch would turn on the internal circuits of the electric pulse provider 20, but would not permit the treatment voltage provided by the electric pulse provider to be fully transmitted to the electrodes 14 on the applicator head 18. Instead, the stand-by off switch would enable the interlock safety switch 36 to function as noted above. In other words, the interlock safety switch 36 would not allow treatment voltage from the electric pulse provider 20 to be transmitted to the electrodes 14, regardless of the disposition of the interlock safety switch 36, unless the standby-off switch was disposed in the "STANDBY" position. It is understood that in certain embodiments of the present invention, the standby-off switch would be placed in the "STANDBY" position just prior to use of the improved TENS unit A to treat a patient.

In an additional alternative embodiment, the improved TENS unit A may be programmed to ramp up the electrical energy at the electrodes 14 from a very low voltage to the final treatment voltage for the patient. This is to say, when applicator head 18 is placed into position against a patient's leg or other body part, the initial voltage potential between the two electrodes 14 may be at or near zero volts. Then, over a specified period of time, the voltage potential between the two electrodes 14 is increased at a specified rate until the final voltage potential is reached. It is understood that the final voltage potential in most embodiments would be the actual treatment pulse as necessary for the treatment of pain for each specific patient. This ramping of the voltage potential between the electrodes 14 would provide a sensitive patient with more comfort during the pain treatment.

Method of Treatment

The improved TENS unit A is intended to be used for the treatment of a wide variety of pain conditions. As noted above, electric pulse provider 20 may have an adjustable output voltage of 0-40 volts/0-80 milliamps and a selectable pulse width of 150/250 microseconds at a frequency of 40 Hz. The output from the electric pulse provider 20 is electrically connected to the set electrodes 14 flanking insulative land 16. As applicator head 18 is pressed against the treatment area, electrodes 14 and land 16 compress the flesh and flatten the nerves 28 under land 16. The electron flow in the pathway 30 under land is channeled in a laminar flow just below the skin and through compressed nerves 28. The skin under the electrodes 14 may be moistened to facilitate the flow of electrons through the skin and pathway 30 under land 16.

With this arrangement it is possible to use low voltage with corresponding low current levels through the high resistance skin to prevent skin burns. For a given current, the power developed across a resistance is proportional to the amount of the resistance. This is why the skin, with its high resistance, can more easily be damaged by electrical current than the low resistance tissue within the body. After the current passes through the larger cross section of the electrodes 14 and through the skin, it recombines just below the compressed skin area in the smaller cross section of pathway 30. This appears to result in a current concentration of at least 3-5 times as it travels through the flesh under the insulating land 16. When the applicator head 18 is pressed against the skin, the three dimensional nerve 28 is entirely compressed within an essentially two dimensional laminar current pathway under the insulating land 16. As a result, the entire three dimensional nerve can be desensitized with an extremely short treatment time.

Referring now to FIGS. 2 and 3, the understood path of the electrical current during treatment with the improved TENS unit A and the effect on the general resistivity of the treated area are illustrated. It is noted that human skin 22 has a resistance of very roughly 6,000 ohms/cm$^2$. That resistivity is pictorially represented in FIGS. 2 and 3 by indicating one 6,000 ohm resistor 24 for each cm$^2$ attached to the electrode surface. In contrast, flesh 26 beneath the skin 22 has a very low resistance compared with the skin. This resistance is varied, but is about 5-40 ohms/cm$^2$. The other ends of the 6,000 ohm resistors 24 are connected to the flesh 26.

In a representative treatment for pain, a set of 0-40 volt pulses are applied by the applicator head 18 at some low frequency and at some convenient pulse width across the electrodes. During that application, the electrical current travels from the anode 14, through the parallel resistors 24 in skin 22, through the flesh 26 in pathway 30 under land 16, through the nerve 28 which is compressed by the insulator land 16, back through the resistors 24 in skin 22 and into the cathode 14. The total current possibly flowing through the compressed nerve 28 is the sum of the currents through the resistors 24.

If the electrodes 14 are made longer as discussed above, the sum of the current is increased through the compressed nerve 28 in pathway 30. Likewise, if the electrodes 14 are shorter in length, the current is reduced through the nerve 28.

It is noted that the above results are generally attributable to the unique design of the applicator head 18 with an insulative land 16 flanked with electrodes 14, all lying in a plane. In other prior art TENS units the individual electrodes that are placed at generally random points on the body and there is no compression of the flesh 26 between the electrodes. Thus there is no concentration of the electrical current more directly to the nerve 28. In other words, one aspect that makes the present invention unique over the prior art is the fact that compressing the nerve 28 with applicator head 18 increases the "effective" current directed toward the nerve 28. In addition, the more direct treatment of the nerve 28 can result in generally reduced treatment time of that nerve than when treated with prior art devices.

Referring now back to FIG. 1, the general treatment of pain using embodiments of improved TENS unit A includes first turning the device on using the selector switch 38A. Then, pulse width selector switch 38B is set to 150 microseconds and the voltage selector switch 38C is set to 4 volts. The applicator head 18 is then is pressed against the moistened skin of the patient over the center of the pain spot. After the flesh 26 under land 16 has been compressed for a moment, the intensity of the treatment can be gradually increased by rotating the intensity control 32. This is done by slowly increase the intensity control 32 for the amplitude until a stinging is felt at the targeted pain center. Normally, holding the applicator head 18 in this position for about 15-45 seconds is usually sufficient, but it may take a longer time and require a higher pulse amplitude for aggressively active pain centers. Longer periods cause no harm but normally are only necessary when treating aggressive pain centers. During treatment the patient will continue to feel a stinging sensation in the symptom center until the pain and pain symptoms from that pain center are eliminated. This stinging is the effect of the ribbon-like flow of pulsating electrical current acting on the flattened nerve 28 in the pain or symptom center. The stinging may feel somewhat like scratching an itch or in aggressively active clusters the stinging may be more intense. This stinging actually feels satisfying because it "scratches the itch" caused by the pain center. Sometimes the portion of the patient's body being compressed by the applicator head 18 will jerk, but pressure should be continued and the applicator head 18 should not be removed during the jerking. When sensitive patients are being treated, embodiments of the present invention as noted above that include a gradual ramping upward of the voltage provided by the electrodes 14 can be used to reduce any discomfort felt by the patient during pain treatments.

The object of improved TENS unit A is to stimulate and confuse the nerve at the pain center which should provide immediate temporary relief from pain symptoms. The process may be repeated for any other pain symptom centers within the problem area. For the pain and nerve problems associated with RLS, Fibromyalgia, and Sciatica, treatment will normally last for 8-36 hours for each symptom center depending on the patient. With strained or pulled muscles, TENS unit A simultaneously relaxes the muscle and desensitizes the painful nerve centers in the muscle strain. This immediately relaxes the muscle which allows normal blood circulation to return to the muscle and enables much faster healing of the strain in the muscle.

In the preceding description, numerous specific details are set forth such as examples of specific components, devices, methods, in order to provide a thorough understanding of embodiments of the present disclosure. It will be apparent to a person of ordinary skill in the art that these specific details need not be employed, and should not be construed to limit the scope of the disclosure. The scope of the invention should be determined by any appended claims and their legal equivalents, rather than by the examples given.

What is claimed is:

1. A transcutaneous electrical nerve stimulation (TENS) unit for treatment of pain comprising:
    a handheld applicator having an applicator head;
    a set of electrodes disposed on the applicator head operatively connected to an electric pulse provider; and,
    an insulative land disposed between the electrodes on the applicator head wherein a surface of the insulating land is generally coplanar with a surface of the set of electrodes.

2. The TENS unit of claim 1 wherein the electrodes and the land are generally rectangular, said electrodes having a length between about 0.25 in. and about 2.5 in. wherein lengths below about 0.25 in. do not provide an effective current density to a treatment area and lengths above about 2.5 in. make it difficult to apply enough pressure on the treatment area.

3. The TENS unit of claim 2 wherein the electrodes flank the insulative land and the land has a length between about 0.5 in. and 3.5 in. wherein lengths below about 0.5 in. result in current flow across the skin in the treatment area and lengths above about 3.5 in. make it difficult to position the applicator head on the nerves in the treatment area.

4. The TENS unit of claim 3 wherein the length of the land is between about 1.25 in. and 1.5 in.

5. The TENS unit of claim 1 wherein the handheld applicator has a paintbrush configuration with a handle portion and a paddle portion, said applicator head being in the paddle portion and said electric pulse provider being disposed in the paddle portion of the handheld applicator.

6. A method for treatment of pain with a transcutaneous electrical nerve stimulation (TENS) unit, said method comprising:
    providing a TENS unit with a handheld applicator with a set of electrodes disposed on an applicator head operatively connected to an electric pulse provider, said handheld applicator further having an insulative land disposed between the electrodes on the applicator head wherein a surface of the insulating land is generally coplanar with a surface of the set of electrodes, said method comprising: selecting a treatment area with a nerve to be stimulated; positioning the applicator head on the treatment area with the nerve positioned under the land;
    pressing the applicator head against the treatment area to compress and flatten the nerve under the land; and,
    applying an electric pulse to the electrodes.

7. The method of claim 6 further providing a TENS unit wherein the electrodes and the land are generally rectangular, said electrodes having a length between about between about 0.25 in. and 2.5 in. and wherein the electrodes flank the insulative land and the land has a length between about 0.5 in. and 3.5 in.

8. The method of claim 7 further comprising applying an electric pulse which starts at a low voltage and ramps to a final treatment voltage.

9. The method of claim 7 wherein the electric pulses are applied until the pain symptoms are eliminated.

10. A transcutaneous electrical nerve stimulation (TENS) unit for treatment of pain comprising:
    a handheld applicator having an applicator head;
    a set of electrodes disposed on the applicator head operatively connected to an electric pulse provider, said electric pulse provider providing:
    an electric pulse at a peak current range of between about 0 and about 80 milliamps;
    an average current of between about 0 and about 0.8 milliamps at 500 ohm resistance
    and a peak voltage range of between about 0 and about 40 volts at 500 ohms resistance; at a voltage of between about 40 volts and about 5 volts;
    at a width of between about 150 microseconds and about 250 microseconds and having a waveform that is an asymmetrical bi-phase square pulse; and,
    an insulating land area disposed between the electrodes wherein a surface of the insulating land area is generally coplanar with the set of electrodes.

11. The TENS unit of claim 10 wherein the handheld applicator further comprises a selector array having at least one of either an on/off selector switch, a pulse width selector switch, an output voltage selector switch, a pulse frequency selector switch, and a pulse current selector switch.

12. The TENS unit of claim 10 wherein the electric pulse provider produces the electric pulse at a maximum charge per pulse of about 20 microcoulombs.

13. The TENS unit of claim 12 wherein the electrical pulse provider is powered by a 9 volt battery disposed within the handheld applicator.

14. The TENS unit of claim 10 wherein the handheld applicator has a paintbrush configuration comprising a handle attached to a paddle, said applicator head within the paddle.

* * * * *